United States Patent [19]

Cawood, Jr. et al.

[11] 4,178,920
[45] Dec. 18, 1979

[54] UROLOGICAL INSTRUMENT WITH DEFLECTING ELEMENT

[75] Inventors: Charles D. Cawood, Jr., Houston, Tex.; John S. Ziegler, Arlington Heights, Ill.

[73] Assignee: American Hospital Supply Corporation, Evanston, Ill.

[21] Appl. No.: 838,989

[22] Filed: Oct. 3, 1977

[51] Int. Cl.² ............................................. A61B 1/00
[52] U.S. Cl. ................................... 128/4; 74/501 R; 74/502; 128/6
[58] Field of Search ............................ 128/17, 4–8, 128/321, 303, 15; 74/501 R, 502, 523

[56] References Cited

U.S. PATENT DOCUMENTS

| | | | |
|---|---|---|---|
| 1,627,941 | 5/1927 | Wappler | 128/7 |
| 2,469,906 | 5/1949 | Wallace | 128/7 |
| 2,532,043 | 11/1950 | Wallace | 128/7 |
| 3,856,016 | 12/1974 | Davis | 128/6 X |
| 4,085,756 | 4/1978 | Weaver | 128/17 X |

FOREIGN PATENT DOCUMENTS

| | | | |
|---|---|---|---|
| 463510 | 3/1950 | Canada | 128/6 |
| 1231169 | 9/1960 | France | 128/6 |

*Primary Examiner*—Clifford D. Crowder
*Assistant Examiner*—Steven A. Bratlie
*Attorney, Agent, or Firm*—Tilton, Fallon, Lungmus & Chestnut

[57] ABSTRACT

A urological instrument for use with an endoscope and an endoscope sheath to facilitate the insertion of one or more catheters or flexible instruments from the bladder into the ureter. The instrument includes an elongated sleeve for receiving the stem of the endoscope, a deflecting element pivotally mounted at the distal end of that sleeve, and a mechanism at the proximal end of the sleeve for operating the deflecting element. The mechanism is spring-loaded so that the deflecting element normally assumes a retracted position generally parallel with the axis of the sleeve. Such mechanism also includes a finger lever for selectively controlling the angular position of the deflecting element. A finger brace projects outwardly from the sleeve on the opposite side from the lever. The construction allows a urologist to operate the mechanism with the same hand used to support the instrument, thereby freeing his other hand for manipulation of the catheter or flexible instrument to be deflected by the pivotal deflecting element.

14 Claims, 6 Drawing Figures

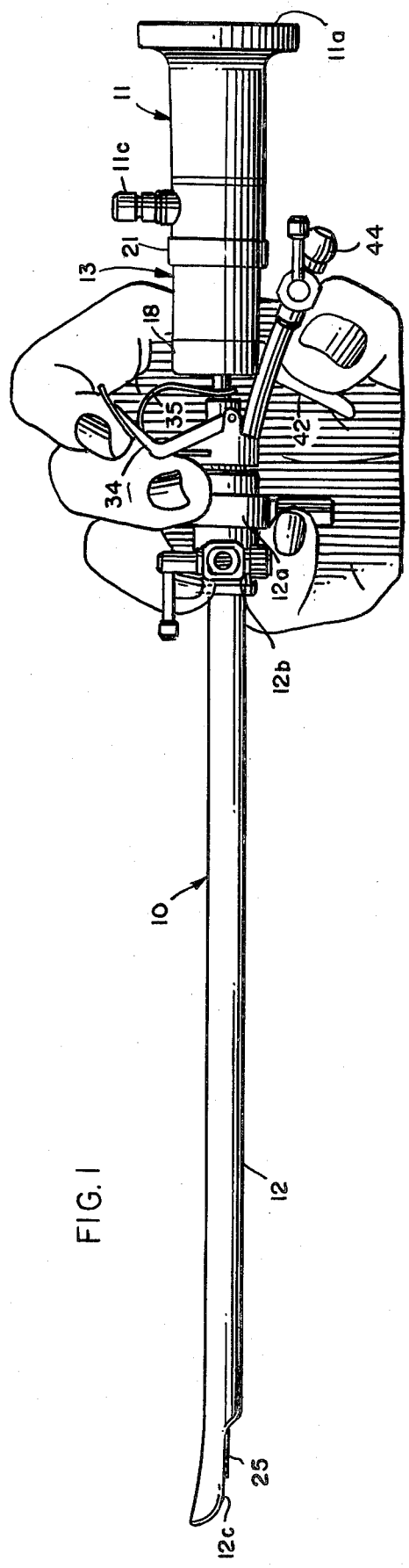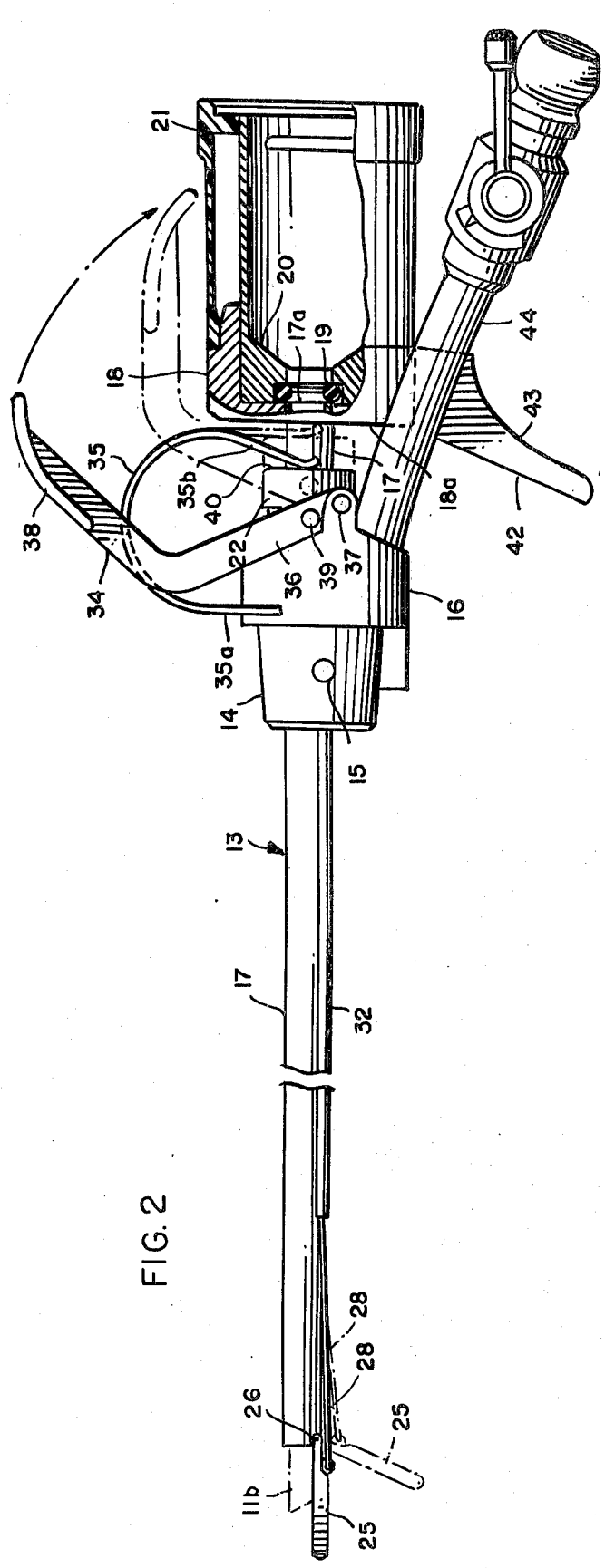

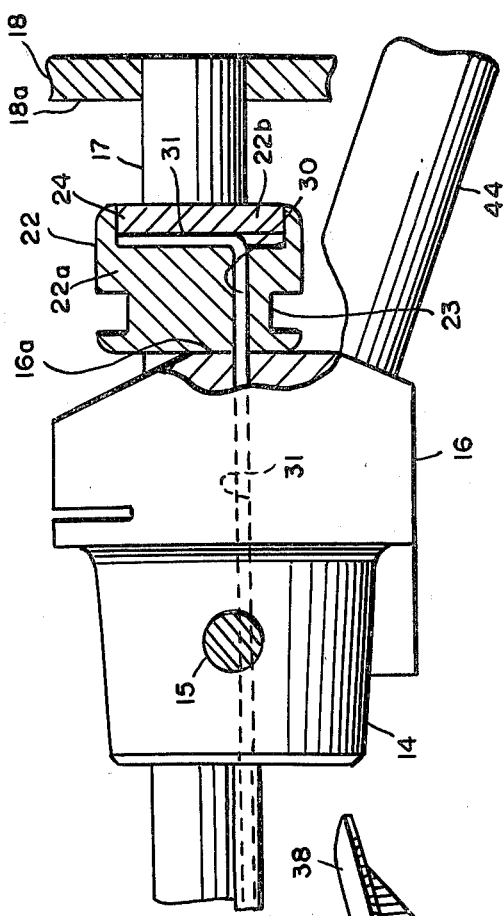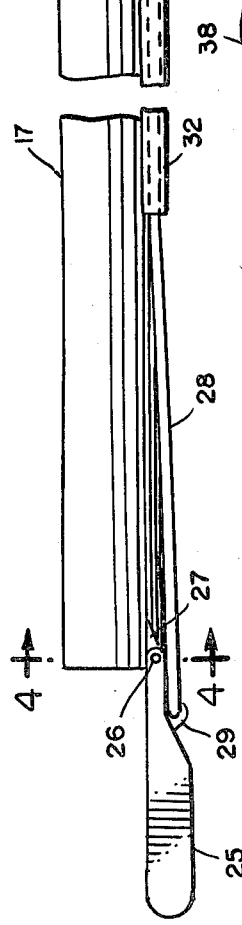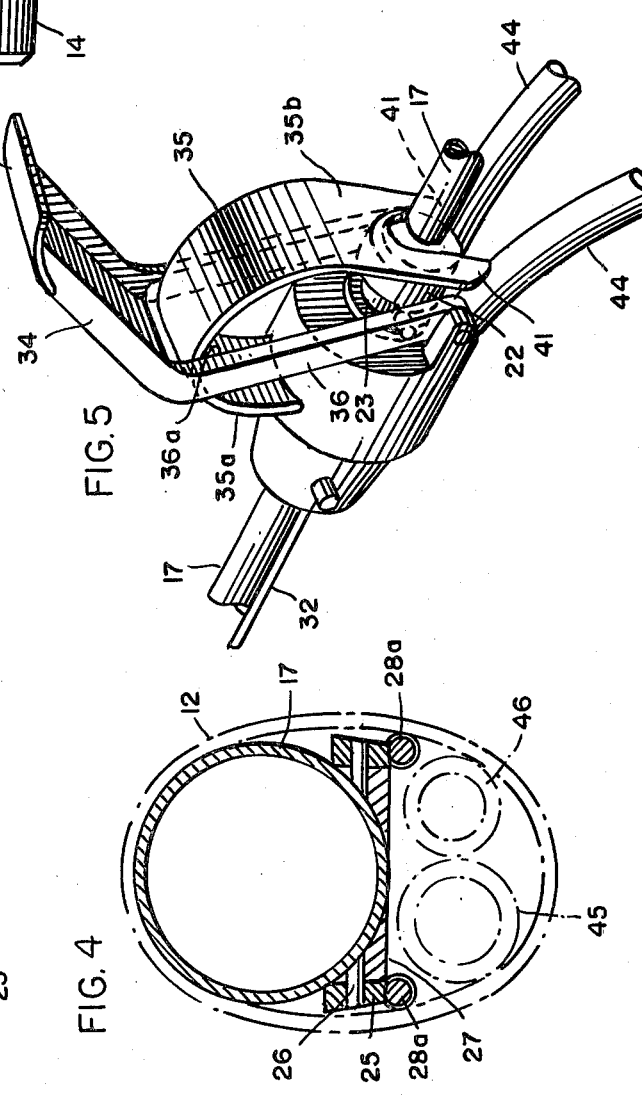

UROLOGICAL INSTRUMENT WITH DEFLECTING ELEMENT

BACKGROUND

Urological instruments equipped with pivotal elements for deflecting a catheter (or some other flexible device such as a stone retriever or miniature flexible instrument) so that it will enter a patient's ureter, or various areas of the bladder, have been well known for many years and are variously identified by designations such as deflecting bridges, Albarran bridges, deflecting lids, catheter deflecting instruments, and the like. Terms such as "bridge" and "lid" are somewhat misleading since the deflecting element of such an instrument functions neither as a bridge nor a lid but rather as a pivotal member which is capable of assuming different angular positions to deflect and guide the tip of a catheter or flexible instrument so that, as viewed by the urologist through the eyepiece of the endoscope, such a tip will be properly positioned for advancement from the bladder into a patient's ureter or to a desired position in the bladder. A conventional instrument typically has at least one operating knob for adjusting the angular position of deflecting element—most commonly, two such knobs are mounted at opposite ends of a single transverse shaft to permit either right or left handed control by the urologist. Whether provided with one knob or two, such an instrument is inherently difficult to manipulate because the urologist must use two hands to perform multiple simultaneous procedures which really require three hands for ease of execution. Specifically, the user (or users) must simultaneously hold the instrument in place, manipulate the control knob for the deflecting element, manually advance the catheter or other device to be directed through the instrument so that its movement can be directed by the deflecting element, and adjust the flow-controlling valves of the instrument. To complicate the procedure even further, all such manipulative steps must be performed while the urologist is looking through the eyepiece of the endoscope to view the operative field.

United States patents illustrating the state of the art are Nos. 1,901,731, 1,595,050, 1,747,407, and 3,886,933. The state of the art is also revealed by catalogs showing and describing urological instruments such as The Surgical Armamentarium, V. Mueller Catalog, Chicago Ill., pages 376, 378, 381–385 (1973).

SUMMARY

An important aspect of this invention lies in the recognition that the conventional knob control for instruments of the type described above is unsatisfactory because it requires two-handed operation—one hand to stabilize the instrument and the other to rotate the knob—thereby making it difficult if not impossible for the urologist to advance one or more catheters, stone-retrieving snares, or other suitable device or devices, through the passages of the instrument. A further aspect of the invention is concerned with the discovery that the deficiencies of prior constructions may be avoided if such an instrument is provided with an operating lever which may be manipulated by the fingers of the same hand used for holding the instrument and if the operating mechanism is spring-loaded to cause return of the lever (and return of the deflecting element) when finger pressure is relieved. Maniuplating of the lever by the hand used for holding the instrument is facilitated by a rigid brace which projects from the instrument on the side opposite from the operating lever. The result is that the urologist may easily hold the cystoscope in one hand, using one finger of that hand to manipulate the operating lever and thereby adjust the angular position of the deflecting element, while using the other hand to advance, twist, or withdraw a catheter, stone-retrieving snare, or flexible instrument, or to manipulate the flow-controlling valves of the cystoscopic instrument.

In brief, the instrument of this invention includes an elongated tubular sleeve for receiving a rigid endoscope or cystoscope. A deflecting element is pivotally connected to the sheath adjacent its distal end and a collar is slidably mounted upon the sheath's proximal end. Wire means operatively connect the deflecting element and the collar so that as the collar slides forwardly and rearwardly (distally and proximally), the deflecting element pivots between first and second positions or any desired position in between. An operating lever, pivotally mounted upon a housing which is secured to the sheath adjacent its proximal end, is movable between raised and lowered positions for shifting the collar and thereby pivoting the deflecting element. A spring is associated with the operating mechanism to urge the lever into a normally extended or raised position and the deflecting element into a retracted position in which it extends generally parallel with the sheath. The sheath is equipped with a finger brace extending radially outwardly from the side opposite from the operating lever. The result is an instrument which may be easily held by and manipulated with the fingers of one hand, leaving the urologist's other hand free for controlling the movement of associated parts or related instruments.

Other features, advantages, and objects of the invention will be apparent from the specification and drawings.

DRAWINGS

FIG. 1 is a side elevational view showing a complete cystoscope assembly in which the instrument of the invention comprises one of the components thereof, the assembly being shown as it might be held for manipulation by a user.

FIG. 2 is an enlarged side elevational view of a urological instrument embodying the invention, such instrument comprising one of the components of the assembly illustrated in FIG. 2.

FIG. 3 is a still further enlarged elevational view, taken partly in section, showing a sub-assembly of an instrument embodying this invention.

FIG. 4 is an enlarged cross sectional view taken along line 4—4 of FIG. 3.

FIG. 5 is a perspective view illustrating details of construction of the lever, the return spring, and related elements.

FIG. 6 is a bottom view of the deflecting element and the wire which interconnects that element to the reciprocable collar.

DETAILED DESCRIPTION

Referring to FIG. 1, the numeral 10 generally designates a complete cystoscope assembly which includes three main components, namely, an endoscope or telescope 11, an endoscope sheath 12, and an operating instrument 13 detachably connected to the sheath and telescope in the relationship illustrated. Both the endoscope (telescope) and the sheath may be entirely conventional in construction. The elongated sheath is generally oval in cross sectional configuration (FIG. 4) and is equipped with a rotatable locking ring 12a for interlocking engagement with the tapered nose 14 and laterally projecting pins 15 of a housing 16 which is part of instrument 13 (FIG. 2). The sheath may also be provided with one or more stopcocks 12b for controlling the flow of fluid into and out of the sheath. At its distal end, the sheath is provided with an enlarged opening 12c which continues for a limited distance along the underside of that sheath.

The telescope or endoscope 11 has an enlarged eyepiece 11a and an elongated stem 11b. The distal end of the stem terminates within the open distal end 12c of the sheath 12. A coupling 11c projects radially from the endoscope for attachment to a suitable light source. As is well known, light-transmitting means, usually in the form of light-conducting fibers, extend from coupling 11b to the distal end of the endoscope to conduct light for illuminating the operative field. The stem or barrel of the endoscope also contains image-transmitting means, ordinarily in the form of oriented light-transmitting fibers or rod lenses, so that the illuminated operative field may be viewed through eyepiece 11a. Since the construction and operation of the endoscope 11 and its sheath 12 may be entirely conventional and are well known in the urological field, a more detailed description of these components is believed unnecessary herein.

Referring to FIG. 2, instrument 13 includes a tubular sleeve 17 for receiving the stem 11b of the endoscope 11. At the proximal end 17a of the sleeve is an enlarged cup-shaped or cylindrical member 18 which is securely affixed to the tubular sleeve. A resilient O-ring 19 is secured within the cup-shaped terminal member by an inner cylindrical member 20. A cylindrical shroud 21, preferably formed of electrically-insulating plastic material, is frictionally secured to the cup-shaped member 18. It is to be understood that the enlarged cavity of the inner member 20 receives a portion of the telescope 11 when the parts are assembled as shown in FIG. 1, the stem of the telescope extending through the passage of sleeve 17 and being frictionally but slidably received by resilient O-ring 19. The locking mechanism for releasably locking the telescope in place is the subject of co-pending co-owned application Ser. No. 881,723, filed Feb. 27, 1978, and since such mechanism forms no part of the present invention further description herein is believed unnecessary.

The housing 16 is rigidly secured to the sleeve 17 adjacent the proximal end of that sleeve but, as shown most clearly in FIGS. 2 and 3, at a short distance in front of (i.e., distal to) the cylindrical cup-shaped member 18. Between the rear (proximal) face 16a of housing 16 and the front (distal) face 18a of member 18 is a collar 22 which is slidably mounted upon sleeve 17. The collar is cylindrical in configuration and is preferably formed in two sections 22a and 22b. The larger distal section 22a has an annular external groove 23. The rear section 22b is in the form of a locking ring which is securely received within recess 24 of front section 2a. In the form shown, section 22b is held in place by a press fit; however, it might be threaded in place if desired.

A deflecting element or member 25 is pivotally connected to the distal end of sleeve 17 by means of pivot pins 26. As shown most clearly in FIG. 4, the pins protrude into a pivot block or tube 27. In manufacturing the instrument, it has been found desirable to secure the pivot block or tube to sleeve 17, extending the block through the sleeve for that purpose, and thereafter remove excess material from within sleeve 17 so that the lumen of the sleeve in the final assembly is unobstructed as shown in FIG. 4. It is to be understood, however, that any other suitable procedures which are well known in the art may be used for pivotally mounting the deflecting element 25.

A U-shaped wire 28, having parallel portions 28a and an intermediate portion 28b, operatively connects the deflecting element 25 and slidable collar 22. The intermediate portion 28b extends through the transverse bore of an enlargement 29 which projects downwardly from the deflecting element at a location distal to and below pivot 26. The proximal ends of portions 28a extend through passages 30 in the collar and have their extreme ends 31 turned at right angles within recess 24 and clamped in place by locking ring 22b (FIG. 3).

The parallel wire portions 28a also extend through passages 31 and through tubes 32 which are welded or otherwise secured to the undersurface of sleeve 17. Tubes 32 perform the dual functions of guiding movement of the connecting wire 28 and protecting the parallel portions of that wire from contact with catheters and other devices inserted through the lumen of the cystoscope sheath 12 beneath sleeve 17.

As the collar is moved forwardly and rearwardly along sleeve 17 the deflecting element pivots between a raised or retracted first position shown in solid lines in FIG. 2 and lowered or extended second position depicted in broken lines in that figure. Movement of the collar is controlled by an operating lever 34 and a spring 35, both of which are mounted upon housing 16 (FIGS. 2 and 5). In the embodiment illustrated, the lever has a pair of depending arms 36 which straddle the collar and which are pivotally connected at their lower ends to the housing by means of pivot pins 37. Above arms 36, the lever angles rearwardly, terminating in a pressure plate portion 38. The range of movement of the lever is depicted in FIG. 2, the lever being movable between the normally raised first position shown in solid lines and the lowered section position illustrated in broken lines. A pair of inwardly projecting pins 39 are provided by arms 36 above the pivot axis of the lever, such pins projecting into the annular groove 23 formed in collar 22. Consequently, when the lever is in its normal raised position, the collar is distally advanced and the deflecting element 25 is raised. As the lever is lowered, the collar is shifted rearwardly to pivot the deflecting element into its lowered second position.

Spring 35 is of inverted U-shaped configuration, having a forward leg 35a which is secured to the housing and a rear leg 35b which bears against the rear surface 40 of the collar and which urges that collar into its forward position, thereby causing the lever to swing into its raised position and to retract the deflecting element into its elevated parallel position. It will be observed from FIG. 5 that the spring extends through an opening 36a between the arms 36 of the lever and that the rear leg 35b of the spring has a pair of projections or fingers 41 at its lower end which are disposed on opposite sides of the sleeve 17 upon which the collar 22 is slidably mounted.

A finger brace 42 is rigidly secured to the member 18 (which is in turn fixed to sleeve 17) and, as shown in FIG. 2, the brace projects downwardly from the instrument in diametric opposition with respect to lever 34.

The rear or proximal side of the brace is curved at 43 to conform generally with the contour of a user's thumb (FIG. 1). The instrument may therefore be easily held by the fingers of one hand, the thumb preferably engaging brace 42 and the middle finger extending above housing 16. Operation of the deflecting element of the instrument is achieved simply by urging lever 34 downwardly with the index finger. When return movement of the deflecting element is required, the user merely relieves the downward finger pressure applied to the lever and spring 35 urges the lever into its original raised position or into any intermediate position desired by merely adjusting finger pressure. The result is an instrument which may be easily held in one hand with the fingers of the same hand being used to control the position of the deflecting element.

In use, with the parts assembled as depicted in FIG. 1, a catheter or other deflectable instrument (such as a stone retrieving instrument or any of the type of miniature instruments commonly referred to as flexible instruments) is inserted forwardly into one of the guide tubes 44 which lead into the space within the cystoscope sheath 17. FIG. 4 illustrates in phantom two such catheters 45 and 46 disposed within the lower portion of the sheath 12. When the tip of such a catheter reaches the distal end of the cystoscope sheath, that tip enters the field of view of telescope 11. By manipulating lever 34, the urologist causes the deflecting element 25 to pivot and thereby deflect or alter the position of the catheter tip. The urologist may thereby direct the tip of the catheter from the bladder into the ureter of the patient. Once the tip has entered the patient's ureter, the catheter may be advanced by feeding that catheter into guide tube 44 of the instrument. Since support of the instrument and manipulation of its deflecting element requires the use of only one hand, the urologist has his other hand free to feed the catheter (or other device) into guide tube 44.

Since the deflecting element is spring loaded into a retracted or parallel position, the possibilities of injury to the urethra that might result when a conventional instrument is withdrawn (and the deflecting element is inadvertently left in an extended or lowered position) are eliminated or greatly reduced. Also, for the same reasons, the risks of damaging the instrument, as by accidentally inserting it into its sheath with the lid extended, are minimized.

While in the foregoing we have disclosed an embodiment of the invention in considerable detail for purposes of illustration, it will be understood by those skilled in the art that many of these details may be varied without departing from the spirit and scope of the invention.

We claim:

1. A urological instrument having an elongated sleeve for receiving the stem of an endoscope; said sleeve having proximal and distal ends; a deflecting element pivotally connected to said sleeve adjacent the distal end thereof; said element being movable between a retracted position generally parallel with said sleeve and an extended position projecting away from said sleeve; an operating lever pivotally supported upon said sleeve adjacent the proximal end thereof for pivotal movement of said lever between first and second positions; means operatively interconnecting said lever and said element for movement of said element between its retracted and extended positions as said lever is shifted between its first and second positions; and spring means urging said lever into its first position; said lever having a free end portion movable towards the axis of said sleeve when the lever pivots from its first position to its second position; said spring means urging said lever to shift said free end portion away from the axis of said sleeve.

2. The instrument of claim 1, in which a finger brace extends away from the axis of said sleeve adjacent the sleeve's proximal end and from a side of said sleeve opposite from said lever; and means connecting said brace to said sleeve.

3. The instrument of claim 2 in which said means connecting said brace to said sleeve comprises a cylindrical member rigidly secured to the proximal end portion of said sleeve; said brace being joined to and extending from said cylindrical member.

4. A urological instrument having an elongated sleeve for receiving the stem of an endoscope; said sleeve having proximal and distal ends; a collar slidably mounted upon said sleeve adjacent the proximal end thereof for axial sliding movement of said collar between first and second positions; a deflecting element pivotally connected to said sleeve adjacent the distal end thereof; said element being movable between a retracted position generally parallel with said sleeve and an extended position projecting away from said sleeve; wire means operatively connecting said element and said collar for retraction of said element as said collar is shifted towards its first position and for extension of said element as said collar is moved towards its second position; an operating lever pivotally mounted upon said sleeve for movement between raised and lowered positions and operatively engaging said collar for shifting said collar axially as said lever is pivoted; and spring means urging said lever into its raised position.

5. The instrument of claim 4 in which a housing is secured to said sleeve adjacent the proximal end thereof; said operating lever being pivotally connected to said housing.

6. The instrument of claim 5 in which said lever has a pair of depending arms pivotally connected at their lower ends to said housing; and means projecting from said arms for operative engagement with said collar.

7. The instrument of claim 6 in which said arms of said lever are spaced apart to define a recess therebetween; said spring means comprising a leaf spring of generally inverted U-shaped configuration extending through said recess; said leaf spring having one end secured to said housing and an opposite end engaging said collar.

8. The instrument of claim 6 in which said means projecting from said arms for engagement with said collar comprises a pair of pins projecting inwardly from said arms; said collar being provided with an external groove for receiving said pins.

9. The instrument of claim 4 in which said sleeve is provided at its proximal end with an enlarged cylindrical member; and a finger brace projecting downwardly from said member in a direction generally opposite from said lever.

10. A urological instrument having an elongated sleeve for receiving the stem of an endoscope; said sleeve having proximal and distal ends; a collar slidably mounted upon said sleeve adjacent the proximal end therefor for axial sliding movement of said collar between first and second positions; and a deflecting element pivotally connected to said sleeve adjacent said distal end; said element being movable between a retracted position generally parallel with said sleeve and an extended position projecting away from said sleeve; wire means operatively connecting said element and said collar for retraction of said element as said collar is shifted towards its first position and for extension of said element as said collar is moved towards its second position; a housing secured to said sleeve; an operating lever pivotally mounted upon said housing for movement between raised and lowered positions; means operatively coupling said lever and said collar so that said element is retracted when said lever is in its raised position and said element is extended when said lever is in its lowered position; and spring means operatively associated with said lever, collar, coupling means, and deflecting element for urging said lever into its raised position and said element into its retracted position.

11. The instrument of claim 10 in which said spring means comprises a leaf spring secured to said housing, said leaf spring having one end thereof secured to said housing and an opposite end engaging said collar.

12. The instrument of claim 10 in which said collar has an external annular groove; said lever being provided with a pair of arms straddling said collar and equipped with pins received in said groove for directing said collar axially upon said sleeve as said lever is pivoted between raised and lowered positions.

13. The instrument of claim 10 in which a finger brace projects downwardly from said sleeve adjacent the proximal end thereof.

14. The instrument of claim 13 in which said brace is rigidly secured to a generally cylindrical member affixed to the proximal end of said sleeve, said brace having an arcuate proximal contour for engagement with a user's thumb.

* * * * *